United States Patent
Matei

(10) Patent No.: US 7,565,204 B2
(45) Date of Patent: Jul. 21, 2009

(54) IMPLANTABLE DEVICE FOR CONTROLLING RECEIVED POWER BY A POWER RECEIVING UNIT THEREIN

(75) Inventor: Eusebiu Matei, Valencia, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 52 days.

(21) Appl. No.: 11/089,833

(22) Filed: Mar. 24, 2005

(65) Prior Publication Data

US 2006/0217785 A1    Sep. 28, 2006

(51) Int. Cl.
*A61N 1/378* (2006.01)
(52) U.S. Cl. .......................................... 607/61
(58) Field of Classification Search ............. 607/60–61, 607/65
See application file for complete search history.

(56) References Cited

U.S. PATENT DOCUMENTS

| 3,236,240 | A | * | 2/1966 | Bradley | 607/40 |
| 3,824,129 | A | * | 7/1974 | Fagan, Jr. | 607/33 |
| 5,324,316 | A | | 6/1994 | Schulman et al. | |
| 5,702,431 | A | * | 12/1997 | Wang et al. | 607/61 |
| 6,185,452 | B1 | | 2/2001 | Schulman et al. | |
| 6,442,434 | B1 | * | 8/2002 | Zarinetchi et al. | 607/61 |
| 6,579,315 | B1 | * | 6/2003 | Weiss | 623/3.27 |
| 6,658,301 | B2 | * | 12/2003 | Loeb et al. | 607/65 |
| 2003/0195581 | A1 | * | 10/2003 | Meadows et al. | 607/29 |

* cited by examiner

*Primary Examiner*—Mark W Bockelman
*Assistant Examiner*—Eric D Bertram
(74) *Attorney, Agent, or Firm*—Malcolm J. Romano

(57) ABSTRACT

An implantable device capable of controlling received power from an external source. The implantable device includes a power receiving unit (PRU) and a control circuit which monitors the voltage across a load and provides a short circuit connection across the PRU when the voltage across the load exceeds a predetermined value.

8 Claims, 4 Drawing Sheets

IMPLANTABLE DEVICE FOR CONTROLLING RECEIVED POWER BY A POWER RECEIVING UNIT THEREIN

FIELD OF THE INVENTION

The field of the invention relates generally to controlling received power in an implantable medical device so as to maintain device temperature within acceptable limits.

DETAILED DESCRIPTION OF THE PREFERRED EMBODIMENTS

The following description is not to be taken in a limiting sense, but is made merely for the purpose of describing the general principles of the embodiments of the invention. The scope of the invention should be determined with reference to the claims.

It is realized that when implantable medical devices (hereafter referred to as "implantable devices") in a patient's body are powered through inductive-coupling to an external power source (hereafter referred to as "external source"), in the process of power transfer there may be undesired heating of the implantable devices that are closer to the surface of the skin and the external source relative to the other implantable devices that are farther away from the external source and more deeply implanted in the body. Any extraneous current flow through the internal impedance of the implanted devices that are more closely coupled with the stronger magnetic field of the external source can cause undesired temperature rise in those implanted devices. It is proposed that a mechanism for controlling the received power from the external source can reduce or eliminate the undesired heating of the implantable devices.

Figure 1:
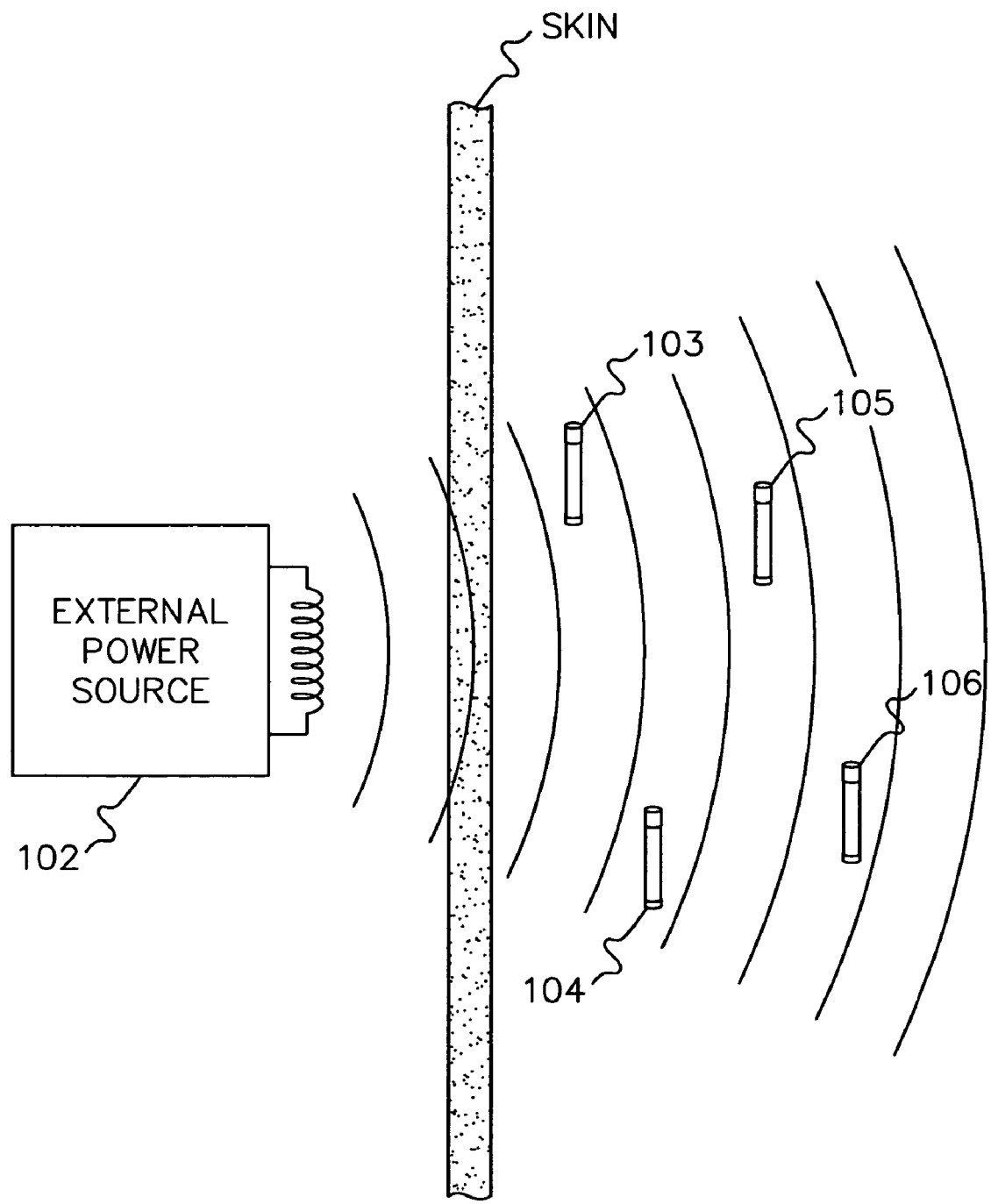
FIG. 1 is an illustration of a system of implanted devices distributed in a body.

FIG. 1 is an illustration of a system of implanted devices in a body. As shown, an external source 102 imparts a larger magnetic field onto the implanted devices 103, 104 that are closer to the external source and a smaller magnetic field onto the implanted devices 105, 106 that are farther away since the magnetic field is attenuated with distance. The implantable devices contemplated in the present embodiments may be microelectronic devices in the form of microstimulators and/or microsensors as described in U.S. Pat. Nos. 5,324,316 and 6,185,452 and which are incorporated by reference herein. These implantable devices may have a rechargeable power source such as a rechargeable battery or a capacitive element contained within them. The power transmission scheme provided from the external source to these implantable devices may be magnetic (inductive) and/or radiofrequency (RF) in nature.

In the exemplary embodiments, an implantable device capable of controlling received power from an external source is described. The external source may comprise a coil that performs the function of a primary winding in an inductively-coupled power transfer system. The implantable device is typically less than 60 mm in axial dimension and less than 6 mm in lateral dimension. Broadly, the exemplary embodiments provide a tuned or resonant circuit comprising an L-C tank of an inductor coil L and a capacitor C, wherein the tuned circuit is rendered ineffective as a result of having a short-circuit connection, by the use of at least one switch, connected across the L-C tank. The transfer of power (energy) from the external source to the power receiving unit is by way of time varying magnetic fields. Due to magnetic coupling, the time varying external source magnetic field induces an electric signal in the power receiving unit inductor coil L. The induced electrical signal has "zero crossings" as a result of the change in potential across the inductor coil L. As will be shown below, an aspect of the exemplary embodiment is to monitor the zero crossings and utilize such for controlling the received power.

Figure 2:
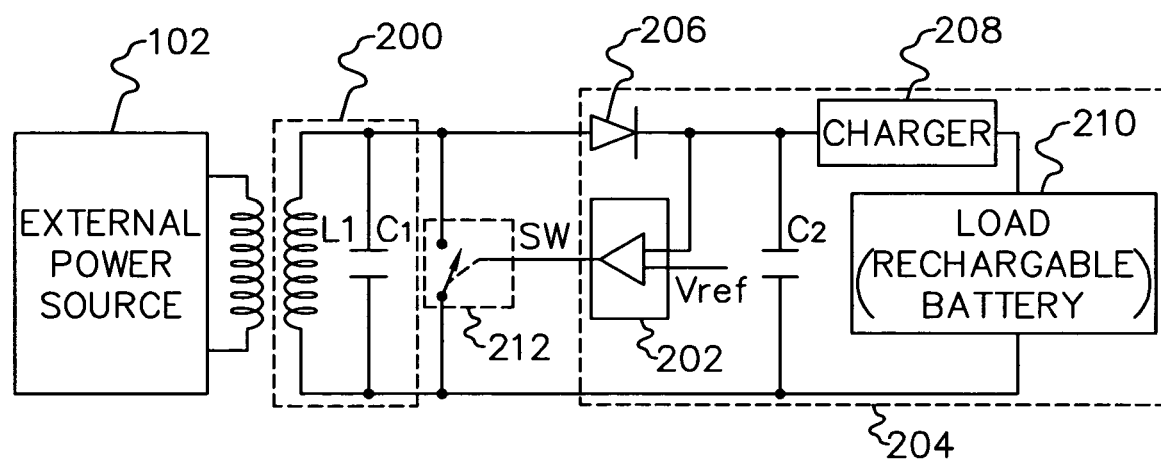
FIG. 2 is an illustration of a first exemplary embodiment of an implantable device in the system of FIG. 1, wherein the implantable device comprises a circuit arrangement capable of controlling received power from the external source.

FIG. 2 is an illustration of a first exemplary embodiment of an implantable device in the system of FIG. 1, wherein the implantable device comprises a circuit arrangement capable of controlling received power from the external source. The exemplary embodiment comprises a power receiving unit (PRU) 200 that is electrically coupled to a switch 212 and wherein the switch 212 is controlled by a controller in a form of a comparator 202. The PRU may be an L-C tank having an inductor/coil L1 and a capacitor C1 as shown in FIG. 2. The PRU is coupled to a load circuit 204 and the PRU provides energy, by means of load charger 208, to a load 210. A capacitor C2 is connected across the series combination of charger 208 and the load 210 and provides a means of energy storage and filtering of the voltage across charger 208 and load 210. The comparator 202 is configured to monitor the voltage across C2 and compare it to a pre-selected reference voltage Vref.

Unless otherwise controlled, the voltage across C1 and thus the voltage across C2 may rise as a function of the strength of the external source magnetic field. An increasing voltage across C1 and thus C2, will typically cause an increase in current in load 210 with a corresponding increase in the temperature of the load 210 and even in coil L1 by virtue of its internal ohmic resistance. Excessive voltages across C1 and C2 may also lead to damage of sensitive electronic circuit components within the implanted device. Accordingly, the reference voltage (Vref) is set in comparator 202 to a value intended to maintain the voltage across C2 and consequently the current through load 210 at or below predetermined values. During the time that the voltage across C2 is below Vref, the comparator 202 causes switch 212 to remain open allowing L1 to receive power from the external source to charge C2 and commence the delivery of power to load 210 through diode 206. Under such protocol, power delivery and thus heat generation in the coil L1 and load 210 can be controlled and maintained within pre-selected ranges.

As shown in FIG. 2, the load circuit 204 comprises a rectifier typically, in the form of a diode 206, which rectifies the induced electrical signal in the PRU; a second storage capacitor C2; a charger circuit 208 that receives the rectified electrical signal and supplies energy to load 210; and a load 210 which may be, but not limited to, a rechargeable battery. In the first exemplary embodiment, the power from the external source is inductively/magnetically coupled to the inductor L1 in the implantable device. The values of the inductor L1 and capacitor C1 (L-C tank) may be selected to provide a tuned circuit having a resonant frequency preferably equal to the frequency of the external source time varying magnetic field, in order to achieve efficient power transfer between the external source and the PRU. The resonant frequency of the tuned circuit is determined by the capacitance value of C1 and the inductance value of L1, which are selected to establish a nominal tuned circuit resonant frequency substantially equal to the frequency of the time varying magnetic field generated by the external source. It is to be understood that tolerance values of L1 and C1 may effect the tuned circuit resonant frequency.

In the present embodiment, the comparator 202 detects the voltage on the storage capacitor C2 and if the voltage is higher than the reference value (Vref), the switch 212 is "closed" to provide a short circuit connection across coil L1. The voltage on the storage capacitor C2 will drop as C2 discharges through charger 208 which in turn delivers energy to the load 210. Concurrently diode 206 will be back-biased and essentially no current from C2 flows back through the short circuit connection. When the voltage on the storage capacitor C2 drops below Vref, the switch 212 is "opened", the short circuit connection is effectively removed and the coil L1 receives energy from the external source to provide current to the load circuit 204. In accordance with the aforementioned embodiment, by controlling the amount of power received by the PRU, the current flow in the load 210 is also controlled, thereby controlling the heat generated in the load thus maintaining the temperature of the load 210 within acceptable limits. It should be noted that typically the coupling between the external source and the coil L1 is weak as a result of the difference in source and coil geometries. Accordingly, the current in coil L1 does not increase noticeably when switch 212 is closed, thereby keeping dissipated power in coil L1 low.

Figure 3:
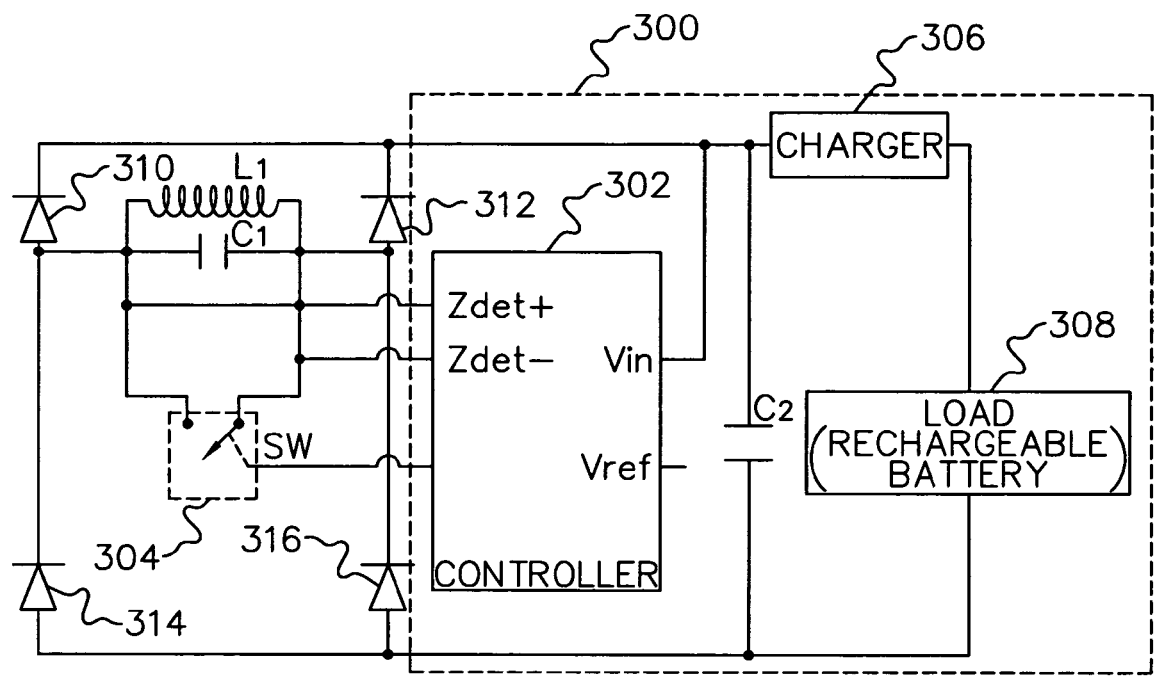
FIG. 3 is an illustration of a second exemplary embodiment of an implantable device in the system of FIG. 1.

FIG. 3 is an illustration of a second exemplary embodiment of an implantable device in the system of FIG. 1. In the second exemplary embodiment, a full wave rectifier is utilized in place of the diode 206 shown in FIG. 2. The full wave rectifier comprises diodes 310, 312, 314, and 316. Accordingly, the voltage appearing across L1 is full wave rectified and applied across load circuit 300. The comparator 302 is configured to monitor the voltage (Vin) across C2 and compare it with the pre-selected reference voltage Vref. Similar to the embodiment of FIG. 2, when the voltage across C2 exceeds Vref, the controller 302 is readied to command switch 304 to "close" to provide a short circuit connection across the PRU.

Advantageously, switch 304 is closed when the voltage across the PRU is at a zero crossing. The voltage across the PRU is monitored by the controller 302 by means of the connection of the controller's Zdet+ and Zdet− inputs to respective sides of the PRU. The use of the Zdet+ and Zdet− inputs in the manner shown, provides an accurate determination of the voltage across the PRU even in view of the isolation of the PRU provided by diodes 310-316. The controller 302 is capable of measuring and detecting the zero crossing of the voltage across coil L1 and thus the voltage across the PRU. It is contemplated that when the controller 302 detects that the voltage on the storage capacitor C2 is higher than the pre-selected Vref, and the voltage across the PRU is at a zero crossing, controller 302 commands the switch 304 to close and thus provide a short-circuit connection across the L-C tank, thereby interrupting the power transfer to the coil L1 and thus interrupting the energy transfer to load circuit 300 and therefore to load 308. It should be noted that by short-circuiting the coil L1 at the zero crossing point, there would be a minimal or no voltage across the coil L1 and the capacitor C1. Accordingly, there would be minimal to no energy stored on the capacitor C1 and dissipated in switch 304 during the transition from open to close positions. As a result, there would be little or a negligible amount of heat generated by the switch 304 due to the intrinsic impedance of the switch 304 during transitions between each position. When the voltage across C2 falls below Vref, the controller 302 causes the switch 304 to "open" thereby removing the short circuit connection across the PRU and returning the receipt of power by the PRU from the external source to normal. Although the switch 212 and 304 are shown as single pole single throw (SPST) devices, it is to be understood that transistor devices may also be used with transistor connections made in a manner know to one skilled in the art.

Figure 4:
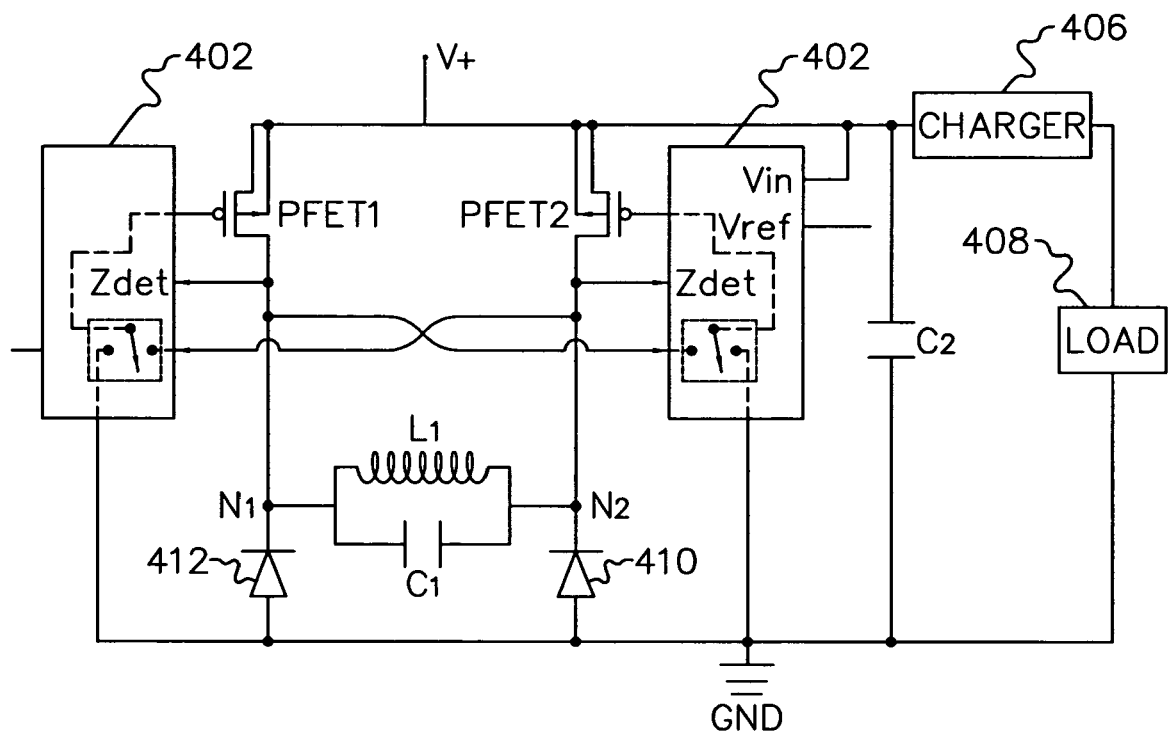
FIG. 4 is an illustration of a third exemplary embodiment of an implantable device in the system of FIG. 1.

FIG. 4 is an illustration of a third exemplary embodiment of an implantable device for controlling received power from the external source wherein the implantable device includes transistors for efficient rectification and for providing a short-circuit connection across the PRU. More specifically and referring to FIG. 4, a controller in a form of a gate driver 402 drives two P-type field-effect-transistors (PFET) namely PFET1 and PFET2 which function as switches for providing a short circuit connection across the L-C tank. The transistors PFET1 and PFET2 may also be used for providing desired rectification in combination with diodes 410 and 412. For example, when rectifying, the gate of each transistor is connected, by means of controller 402, to the drain of the other transistor. If the voltage on node N1 for example, is greater than that on node N2 and the voltage difference between N1 and N2 is larger than V+ (the voltage on C2), then diode 410 will conduct since node N2 will have a negative potential when compared to ground (GND). Since the gate of PFET1 is connected to node N2 by means of controller 402, PFET1 will be conducting (ON) thereby connecting node N1 to V+. Since the gate of PFET2 is connected to node N1 and since it has the same potential (V+) as the source of PFET2, PFET2 is non-conducting (OFF) and diode 412 is reverse-biased and therefore non-conducting. Current flows through diode 410, the L-C tank, PFET1 and to the load 408. If the voltage on the L-C tank changes polarity, then the current will change to flow through diode 412 and PFET2. If the voltage on C2 is higher than Vref, then controller 402 will cause the gates of both PFET1 and PFET2 to be connected to GND, both transistors will be conducting, and the L-C tank will be short-circuited.

The controller 402 is capable of detecting a zero crossing of the voltage across the L-C tank through the inputs denoted as Zdet. Moreover, the controller 402 is configured for detecting the voltage on the storage capacitor C2 and in a manner as previously described, cause a short circuit connection across the L-C tank when the voltage across C2 exceeds Vref and the voltage across the L-C tank goes through a zero crossing.

In an alternative aspect, it is contemplated that diodes 410 and 412 can be replaced by NFET transistors with connection to controller 402 for control of their operation. Furthermore, the selection of PFET transistors corresponds to the polarity of the power supply voltage V+. If a negative potential is utilized, then the use of NFET transistors is contemplated.

In all of the above-described embodiments, by controlling the received power and consequently the current flow, the heat generated in the implantable device is reduced and maintained within acceptable limits.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable device capable of controlling received power from an external source comprising:
   a power receiving unit (PRU) adapted to receive power from an external power source by means of magnetic coupling to said external power source, said PRU comprising a resonant circuit comprising at least an inductor and a capacitor and wherein the external power source induces a time varying electrical signal in the inductor providing thereby a time varying PRU signal, said time varying electrical signal characterized as having zero voltage crossings;
   a load circuit coupled to the PRU and configured to receive power therefrom;
   a switch circuit interconnected between the PRU and the load circuit, the switch circuit adapted to interrupt the transfer of power from the PRU to the load circuit, wherein the switch circuit provides a short circuit connection across the PRU to thereby interrupt power transfer from the PRU to the load circuit; and
   a voltage comparator operatively coupled to the switch circuit and configured to monitor the voltage across the load circuit wherein the comparator circuit further comprises a zero voltage crossing detector whereby the comparator circuit causes the switch circuit to interrupt the power transfer from the PRU to the load circuit as a function of a detected zero voltage crossing.

2. The implantable device of claim 1 wherein the comparator causes the switch circuit to interrupt the transfer of power from the PRU to the load circuit when the voltage across the load circuit exceeds a reference value.

3. The implantable device of claim 1 wherein the switch circuit comprises a single pole single throw (SPST) switch coupled across the PRU such that in closed position the SPST provides a short circuit connection across the PRU.

4. The implantable device of claim 1 wherein the switch circuit comprises a transistor device coupled across the PRU such that when activated the transistor device provides a short circuit connection across the PRU.

5. The implantable device of claim 1 wherein the comparator circuit causes the switch circuit to interrupts the power transfer from the PRU to the load circuit when a zero voltage crossing is detected and the voltage across the load circuit exceeds a reference value.

6. The implantable device of claim 1 wherein
   the implantable device further comprising a full wave rectifier circuit interposed between the PRU and the load circuit to provide full wave rectification of the PRU time varying electrical signal.

7. The implantable device of claim 6 wherein the full wave rectifier circuit comprises at least two transistors arranged to provide rectification of the PRU time varying signal and upon detection of a zero crossing to provide a short circuit connection across the PRU.

8. The implantable device of claim 1 wherein the external source provides a time varying magnetic field at a predetermined frequency and wherein the PRU comprises a parallel inductor-capacitor tank circuit, the values of the inductor and capacitor selected to provide a tank circuit resonant frequency being substantially equal to the frequency of the time varying magnetic field.

* * * * *